(12) United States Patent
Starksen

(10) Patent No.: US 7,922,762 B2
(45) Date of Patent: *Apr. 12, 2011

(54) DEVICES AND METHODS FOR CARDIAC ANNULUS STABILIZATION AND TREATMENT

(75) Inventor: Niel F. Starksen, Los Altos Hills, CA (US)

(73) Assignee: Guided Delivery Systems Inc., Santa Clara, CA (US)

( * ) Notice: Subject to any disclaimer, the term of this patent is extended or adjusted under 35 U.S.C. 154(b) by 133 days.

This patent is subject to a terminal disclaimer.

(21) Appl. No.: 12/132,375

(22) Filed: Jun. 3, 2008

(65) Prior Publication Data

US 2008/0234815 A1 Sep. 25, 2008

Related U.S. Application Data

(62) Division of application No. 10/656,797, filed on Sep. 4, 2003, now Pat. No. 7,753,922.

(51) Int. Cl.
*A61F 2/24* (2006.01)

(52) U.S. Cl. ....... 623/2.11; 623/2.36; 606/139; 606/151

(58) Field of Classification Search .................. 606/144, 606/139, 151; 623/2.11, 2.38, 2.39, 2.4, 623/2.41, 2.36

See application file for complete search history.

(56) References Cited

U.S. PATENT DOCUMENTS

| | | | |
|---|---|---|---|
| 2,108,206 A | 2/1938 | Meeker | |
| 3,656,185 A | 4/1972 | Carpentier | |
| 3,727,614 A | 4/1973 | Kniazuk | |
| 3,773,034 A | 11/1973 | Burns et al. | |
| 3,961,419 A | 6/1976 | Schwartz | |
| 3,976,079 A | 8/1976 | Samuels et al. | |
| 4,014,492 A | 3/1977 | Rothfuss | |
| 4,034,473 A | 7/1977 | May | |
| 4,042,979 A | 8/1977 | Angell | |
| 4,043,504 A | 8/1977 | Hueil et al. | |
| 4,053,979 A | 10/1977 | Tuthill et al. | |
| 4,055,861 A | 11/1977 | Carpentier et al. | |

(Continued)

FOREIGN PATENT DOCUMENTS

EP 0 669 101 A1 8/1995

(Continued)

OTHER PUBLICATIONS

European Examination Communication mailed on Dec. 8, 2009, for EP Application No. 06 837 222.6 filed on Nov. 8, 2006, three pages.

(Continued)

*Primary Examiner* — Eduardo C Robert
*Assistant Examiner* — Katherine M Dowe
(74) *Attorney, Agent, or Firm* — Morrison & Foerster LLP

(57) ABSTRACT

Devices and methods generally provide enhanced stabilization, exposure and/or treatment of a cardiac valve annulus. Methods generally involve introducing a stabilizing member beneath one or more leaflets of a heart valve to engage the annulus at an intersection between the leaflets and the interior ventricular wall of the heart. Force is then applied to the stabilizing member to stabilize and/or expose the valve annulus. In some embodiments, the stabilizing member may include a series of hydraulically driven tethered anchors, such as hooks or clips, for engaging and cinching valve annulus tissue to decrease the diameter of a regurgitant valve. Alternatively, other treatments may be delivered by a stabilizing member, such as radiofrequency energy, drugs, bulking agents or shape memory stents. A second stabilizing member may also be introduced above the leaflets for further stabilization.

3 Claims, 9 Drawing Sheets

U.S. PATENT DOCUMENTS

| | | |
|---|---|---|
| 4,069,825 A | 1/1978 | Akiyama |
| 4,290,151 A | 9/1981 | Massana |
| 4,384,406 A | 5/1983 | Tischlinger |
| 4,445,892 A | 5/1984 | Hussein et al. |
| 4,489,446 A | 12/1984 | Reed |
| 4,494,542 A | 1/1985 | Lee |
| 4,619,247 A | 10/1986 | Inoue et al. |
| 4,700,250 A | 10/1987 | Kuriyama |
| 4,726,371 A | 2/1988 | Gibbens |
| 4,758,221 A | 7/1988 | Jureidini |
| 4,784,133 A | 11/1988 | Mackin |
| 4,845,851 A | 7/1989 | Warthen |
| 4,848,341 A | 7/1989 | Ahmad |
| 4,850,354 A | 7/1989 | McGurk-Burleson et al. |
| 4,961,738 A | 10/1990 | Mackin |
| 4,969,893 A | 11/1990 | Swor |
| 4,976,710 A | 12/1990 | Mackin |
| 5,053,047 A | 10/1991 | Yoon |
| 5,064,431 A | 11/1991 | Gilbertson et al. |
| 5,078,731 A | 1/1992 | Hayhurst |
| 5,084,058 A | 1/1992 | Li |
| 5,103,804 A | 4/1992 | Abele et al. |
| 5,133,723 A | 7/1992 | Li et al. |
| 5,221,255 A | 6/1993 | Mahurkar et al. |
| 5,242,456 A | 9/1993 | Nash et al. |
| 5,242,457 A | 9/1993 | Akopov et al. |
| 5,257,975 A | 11/1993 | Foshee |
| 5,312,341 A | 5/1994 | Turi |
| 5,324,298 A | 6/1994 | Phillips et al. |
| 5,346,500 A | 9/1994 | Suchart |
| 5,358,479 A | 10/1994 | Wilson |
| 5,358,514 A | 10/1994 | Schulman et al. |
| 5,364,407 A | 11/1994 | Poll |
| 5,366,479 A | 11/1994 | McGarry et al. |
| 5,368,591 A | 11/1994 | Lennox et al. |
| 5,383,905 A | 1/1995 | Golds et al. |
| 5,409,483 A | 4/1995 | Campbell et al. |
| 5,409,499 A | 4/1995 | Yi |
| 5,417,700 A | 5/1995 | Egan |
| 5,423,837 A | 6/1995 | Mericle et al. |
| 5,437,680 A | 8/1995 | Yoon |
| 5,439,470 A | 8/1995 | Li |
| 5,450,860 A | 9/1995 | O'Connor |
| 5,452,513 A | 9/1995 | Zinnbauer et al. |
| 5,474,572 A | 12/1995 | Hayhurst |
| 5,520,702 A | 5/1996 | Sauer et al. |
| 5,522,873 A | 6/1996 | Jackman et al. |
| 5,524,630 A | 6/1996 | Crowley |
| 5,527,323 A | 6/1996 | Jervis et al. |
| 5,531,686 A | 7/1996 | Lundquist et al. |
| 5,545,134 A | 8/1996 | Hilaire et al. |
| 5,545,168 A | 8/1996 | Burke |
| 5,565,122 A | 10/1996 | Zinnbauer et al. |
| 5,571,215 A | 11/1996 | Sterman et al. |
| 5,591,194 A | 1/1997 | Berthiaume |
| 5,626,614 A | 5/1997 | Hart |
| 5,630,824 A | 5/1997 | Hart |
| 5,643,289 A | 7/1997 | Sauer et al. |
| 5,669,917 A | 9/1997 | Sauer et al. |
| 5,674,279 A | 10/1997 | Wright et al. |
| 5,690,655 A | 11/1997 | Hart et al. |
| 5,709,695 A | 1/1998 | Northrup, III |
| 5,716,370 A | 2/1998 | Williamson, IV et al. |
| 5,718,725 A | 2/1998 | Sterman et al. |
| 5,725,542 A | 3/1998 | Yoon |
| 5,735,290 A | 4/1998 | Sterman et al. |
| 5,741,260 A | 4/1998 | Songer et al. |
| 5,741,301 A | 4/1998 | Pagedas |
| 5,752,518 A | 5/1998 | McGee et al. |
| 5,752,964 A | 5/1998 | Mericle |
| 5,752,966 A | 5/1998 | Chang |
| 5,755,730 A | 5/1998 | Swain et al. |
| 5,766,240 A | 6/1998 | Johnson |
| 5,769,812 A | 6/1998 | Stevens et al. |
| 5,782,861 A | 7/1998 | Cragg et al. |
| 5,810,848 A | 9/1998 | Hayhurst |
| 5,810,853 A | 9/1998 | Yoon |
| 5,817,107 A | 10/1998 | Schaller |
| 5,827,171 A | 10/1998 | Dobak, III et al. |
| 5,843,169 A | 12/1998 | Taheri |
| 5,848,969 A | 12/1998 | Panescu et al. |
| 5,860,992 A | 1/1999 | Daniel et al. |
| 5,860,993 A | 1/1999 | Thompson et al. |
| 5,868,733 A | 2/1999 | Ockuly et al. |
| 5,879,371 A | 3/1999 | Gardiner et al. |
| 5,885,238 A | 3/1999 | Stevens et al. |
| 5,888,240 A | 3/1999 | Carpentier et al. |
| 5,902,321 A | 5/1999 | Caspari et al. |
| 5,904,651 A | 5/1999 | Swanson et al. |
| 5,919,208 A | 7/1999 | Valenti |
| 5,935,149 A | 8/1999 | Ek |
| 5,947,983 A | 9/1999 | Solar et al. |
| 5,961,440 A | 10/1999 | Schweich, Jr. et al. |
| 5,961,539 A | 10/1999 | Northrup, III et al. |
| 5,972,004 A | 10/1999 | Williamson, IV et al. |
| 5,989,284 A | 11/1999 | Laufer |
| 5,991,650 A | 11/1999 | Swanson et al. |
| 6,010,531 A | 1/2000 | Donlon et al. |
| 6,015,428 A | 1/2000 | Pagedas |
| 6,045,497 A | 4/2000 | Schweich, Jr. et al. |
| 6,050,936 A | 4/2000 | Schweich, Jr. et al. |
| 6,066,160 A | 5/2000 | Colvin et al. |
| 6,074,401 A | 6/2000 | Gardiner et al. |
| 6,077,214 A | 6/2000 | Mortier et al. |
| 6,077,989 A | 6/2000 | Kandel et al. |
| 6,099,553 A | 8/2000 | Hart et al. |
| 6,125,852 A | 10/2000 | Stevens et al. |
| 6,149,658 A | 11/2000 | Gardiner et al. |
| 6,162,168 A | 12/2000 | Schweich, Jr. et al. |
| 6,165,183 A | 12/2000 | Kuehn et al. |
| 6,171,329 B1 | 1/2001 | Shaw et al. |
| 6,197,017 B1 | 3/2001 | Brock et al. |
| 6,221,084 B1 | 4/2001 | Fleenor |
| 6,228,096 B1 | 5/2001 | Marchand |
| 6,250,308 B1 | 6/2001 | Cox |
| 6,254,620 B1 | 7/2001 | Koh et al. |
| 6,258,118 B1 | 7/2001 | Baum et al. |
| 6,260,552 B1 | 7/2001 | Mortier et al. |
| 6,269,819 B1 | 8/2001 | Oz et al. |
| 6,283,993 B1 | 9/2001 | Cosgrove et al. |
| 6,306,149 B1 | 10/2001 | Meade |
| 6,312,447 B1 | 11/2001 | Grimes |
| 6,328,727 B1 | 12/2001 | Frazier et al. |
| 6,332,893 B1 | 12/2001 | Mortier et al. |
| 6,355,030 B1 | 3/2002 | Aldrich et al. |
| 6,378,289 B1 | 4/2002 | Trudeau et al. |
| 6,391,048 B1 | 5/2002 | Ginn et al. |
| 6,409,743 B1 | 6/2002 | Fenton, Jr. |
| 6,423,088 B1 | 7/2002 | Fenton, Jr. |
| 6,432,123 B2 | 8/2002 | Schwartz et al. |
| 6,461,327 B1 | 10/2002 | Addis et al. |
| 6,514,265 B2 | 2/2003 | Ho et al. |
| 6,524,338 B1 | 2/2003 | Gundry |
| 6,533,753 B1 | 3/2003 | Haarstad et al. |
| 6,551,332 B1 | 4/2003 | Nguyen et al. |
| 6,575,971 B2 | 6/2003 | Hauck et al. |
| 6,602,288 B1 | 8/2003 | Cosgrove et al. |
| 6,602,289 B1 | 8/2003 | Colvin et al. |
| 6,607,541 B1 | 8/2003 | Gardiner et al. |
| 6,613,059 B2 | 9/2003 | Schaller et al. |
| 6,619,291 B2 | 9/2003 | Hlavka et al. |
| 6,626,899 B2 | 9/2003 | Houser et al. |
| 6,629,534 B1 | 10/2003 | St. Goar et al. |
| 6,641,593 B1 | 11/2003 | Schaller et al. |
| 6,648,903 B1 | 11/2003 | Pierson, III |
| 6,651,671 B1 | 11/2003 | Donlon et al. |
| 6,655,386 B1 | 12/2003 | Makower et al. |
| 6,669,687 B1 | 12/2003 | Saadat |
| 6,676,702 B2 | 1/2004 | Mathis |
| 6,689,164 B1 | 2/2004 | Seguin |
| 6,699,263 B2 | 3/2004 | Cope |
| 6,702,826 B2 | 3/2004 | Liddicoat et al. |
| 6,716,243 B1 | 4/2004 | Colvin et al. |
| 6,718,985 B2 | 4/2004 | Hlavka et al. |
| 6,723,107 B1 | 4/2004 | Skiba et al. |
| 6,733,509 B2 | 5/2004 | Nobles et al. |
| 6,752,813 B2 | 6/2004 | Goldfarb et al. |

| Patent/Publication | Date | Inventors |
|---|---|---|
| 6,790,231 B2 | 9/2004 | Liddicoat et al. |
| 6,793,618 B2 | 9/2004 | Schweich, Jr. et al. |
| 6,811,560 B2 | 11/2004 | Jones et al. |
| 6,908,424 B2 | 6/2005 | Mortier et al. |
| 6,923,818 B2 | 8/2005 | Muramatsu et al. |
| 6,932,792 B1 | 8/2005 | St. Goar et al. |
| 6,986,775 B2 | 1/2006 | Morales et al. |
| 6,991,643 B2 | 1/2006 | Saadat |
| 6,997,931 B2 | 2/2006 | Sauer et al. |
| 7,004,958 B2 | 2/2006 | Adams et al. |
| 7,037,334 B1 | 5/2006 | Hlavka et al. |
| 7,044,957 B2 | 5/2006 | Foerster et al. |
| 7,048,754 B2 | 5/2006 | Martin et al. |
| 7,101,395 B2 | 9/2006 | Tremulis et al. |
| 7,125,421 B2 | 10/2006 | Tremulis et al. |
| 7,166,127 B2 | 1/2007 | Spence et al. |
| 7,186,262 B2 | 3/2007 | Saadat |
| 7,189,199 B2 | 3/2007 | McCarthy et al. |
| 7,235,086 B2 | 6/2007 | Sauer et al. |
| 7,241,310 B2 | 7/2007 | Taylor et al. |
| 7,344,544 B2 | 3/2008 | Bender et al. |
| 7,452,325 B2 | 11/2008 | Schaller |
| 7,588,582 B2 | 9/2009 | Starksen et al. |
| 7,618,449 B2 | 11/2009 | Tremulis et al. |
| 7,666,193 B2 | 2/2010 | Starksen et al. |
| 7,727,247 B2 | 6/2010 | Kimura et al. |
| 7,753,922 B2 | 7/2010 | Starksen |
| 7,758,637 B2 | 7/2010 | Starksen et al. |
| 2001/0005787 A1 | 6/2001 | Oz et al. |
| 2001/0014800 A1 | 8/2001 | Frazier et al. |
| 2001/0023332 A1 | 9/2001 | Hahnen |
| 2001/0031979 A1 | 10/2001 | Ricci |
| 2002/0013621 A1 | 1/2002 | Stobie et al. |
| 2002/0026201 A1 | 2/2002 | Foerster et al. |
| 2002/0029080 A1 | 3/2002 | Mortier et al. |
| 2002/0035361 A1 | 3/2002 | Houser et al. |
| 2002/0042621 A1 | 4/2002 | Liddicoat et al. |
| 2002/0065536 A1 | 5/2002 | Hart et al. |
| 2002/0072757 A1 | 6/2002 | Ahmed et al. |
| 2002/0087048 A1 | 7/2002 | Brock et al. |
| 2002/0087049 A1 | 7/2002 | Brock et al. |
| 2002/0087148 A1 | 7/2002 | Brock et al. |
| 2002/0087169 A1 | 7/2002 | Brock et al. |
| 2002/0095167 A1 | 7/2002 | Liddicoat et al. |
| 2002/0095175 A1 | 7/2002 | Brock et al. |
| 2002/0138044 A1 | 9/2002 | Streeter et al. |
| 2002/0156526 A1 | 10/2002 | Hlavka et al. |
| 2002/0161378 A1 | 10/2002 | Downing |
| 2002/0165486 A1 | 11/2002 | Bertolero et al. |
| 2002/0173841 A1 | 11/2002 | Ortiz et al. |
| 2002/0193815 A1 | 12/2002 | Foerster et al. |
| 2003/0009196 A1 | 1/2003 | Peterson |
| 2003/0018358 A1 | 1/2003 | Saadat |
| 2003/0032979 A1 | 2/2003 | Mortier et al. |
| 2003/0033006 A1 | 2/2003 | Phillips et al. |
| 2003/0060813 A1 | 3/2003 | Loeb et al. |
| 2003/0069593 A1 | 4/2003 | Tremulis et al. |
| 2003/0074012 A1 | 4/2003 | Nguyen et al. |
| 2003/0078465 A1 | 4/2003 | Pai et al. |
| 2003/0078603 A1 | 4/2003 | Schaller et al. |
| 2003/0093118 A1 | 5/2003 | Ho et al. |
| 2003/0105520 A1 | 6/2003 | Alferness et al. |
| 2003/0125739 A1 | 7/2003 | Bagga et al. |
| 2003/0125767 A1 | 7/2003 | Collier et al. |
| 2003/0130731 A1 | 7/2003 | Vidlund et al. |
| 2003/0144697 A1 | 7/2003 | Mathis et al. |
| 2003/0158464 A1 | 8/2003 | Bertolero |
| 2003/0158581 A1 | 8/2003 | Levinson |
| 2003/0167062 A1 | 9/2003 | Gambale et al. |
| 2003/0167071 A1 | 9/2003 | Martin et al. |
| 2003/0199974 A1 | 10/2003 | Lee et al. |
| 2003/0220685 A1 | 11/2003 | Hlavka et al. |
| 2003/0225420 A1 | 12/2003 | Wardle |
| 2003/0233105 A1 | 12/2003 | Gayton |
| 2003/0233142 A1 | 12/2003 | Morales et al. |
| 2003/0236535 A1 | 12/2003 | Onuki et al. |
| 2004/0003819 A1 | 1/2004 | St. Goar et al. |
| 2004/0019378 A1 | 1/2004 | Hlavka et al. |
| 2004/0030382 A1 | 2/2004 | St. Goar et al. |
| 2004/0039442 A1 | 2/2004 | St. Goar et al. |
| 2004/0092962 A1 | 5/2004 | Thornton et al. |
| 2004/0093024 A1 | 5/2004 | Lousararian et al. |
| 2004/0097788 A1 | 5/2004 | Mourlas et al. |
| 2004/0122450 A1 | 6/2004 | Oren et al. |
| 2004/0172046 A1 | 9/2004 | Hlavka et al. |
| 2004/0181238 A1 | 9/2004 | Zarbatany et al. |
| 2004/0193191 A1 | 9/2004 | Starksen et al. |
| 2004/0204724 A1 | 10/2004 | Kissel et al. |
| 2004/0210238 A1 | 10/2004 | Nobles et al. |
| 2004/0236372 A1 | 11/2004 | Anspach, III et al. |
| 2004/0236419 A1 | 11/2004 | Milo |
| 2004/0243227 A1 | 12/2004 | Starksen et al. |
| 2005/0055052 A1 | 3/2005 | Lombardo et al. |
| 2005/0055087 A1 | 3/2005 | Starksen |
| 2005/0065550 A1 | 3/2005 | Starksen et al. |
| 2005/0080454 A1 | 4/2005 | Drews et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107871 A1 | 5/2005 | Realyvasquez et al. |
| 2005/0119523 A1 | 6/2005 | Starksen et al. |
| 2005/0119673 A1 | 6/2005 | Gordon et al. |
| 2005/0184122 A1 | 8/2005 | Hlavka et al. |
| 2005/0192599 A1 | 9/2005 | Demarais |
| 2005/0192629 A1 | 9/2005 | Saadat et al. |
| 2005/0197694 A1 | 9/2005 | Pai et al. |
| 2005/0216078 A1 | 9/2005 | Starksen et al. |
| 2005/0228452 A1 | 10/2005 | Mourlas et al. |
| 2005/0251157 A1 | 11/2005 | Saadat et al. |
| 2005/0251159 A1 | 11/2005 | Ewers et al. |
| 2005/0251166 A1 | 11/2005 | Vaughan et al. |
| 2005/0251177 A1 | 11/2005 | Saadat et al. |
| 2005/0251205 A1 | 11/2005 | Ewers et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0273138 A1 | 12/2005 | To et al. |
| 2005/0277966 A1 | 12/2005 | Ewers et al. |
| 2005/0277981 A1 | 12/2005 | Maahs et al. |
| 2005/0277983 A1 | 12/2005 | Saadat et al. |
| 2006/0015144 A1 | 1/2006 | Burbank et al. |
| 2006/0025750 A1 | 2/2006 | Starksen et al. |
| 2006/0025784 A1 | 2/2006 | Starksen et al. |
| 2006/0025787 A1 | 2/2006 | Morales et al. |
| 2006/0058817 A1 | 3/2006 | Starksen et al. |
| 2006/0069429 A1 | 3/2006 | Spence et al. |
| 2006/0122633 A1 | 6/2006 | To et al. |
| 2006/0129188 A1 | 6/2006 | Starksen et al. |
| 2006/0178682 A1 | 8/2006 | Boehlke |
| 2006/0184203 A1 | 8/2006 | Martin et al. |
| 2006/0190030 A1 | 8/2006 | To et al. |
| 2006/0241656 A1 | 10/2006 | Starksen et al. |
| 2006/0264975 A1 | 11/2006 | Pipenhagen et al. |
| 2006/0271101 A1 | 11/2006 | Saadat et al. |
| 2006/0287661 A1 | 12/2006 | Bolduc et al. |
| 2007/0005081 A1 | 1/2007 | Findlay, III et al. |
| 2007/0005394 A1 | 1/2007 | Bleyendaal et al. |
| 2007/0010857 A1 | 1/2007 | Sugimoto et al. |
| 2007/0032820 A1 | 2/2007 | Chin-Chen et al. |
| 2007/0038293 A1 | 2/2007 | St.Goar et al. |
| 2007/0049942 A1 | 3/2007 | Hindrichs et al. |
| 2007/0051377 A1 | 3/2007 | Douk et al. |
| 2007/0055206 A1 | 3/2007 | To et al. |
| 2007/0112424 A1 | 5/2007 | Spence et al. |
| 2008/0045977 A1 | 2/2008 | To et al. |
| 2008/0045982 A1 | 2/2008 | To et al. |
| 2008/0045983 A1 | 2/2008 | To et al. |
| 2008/0051810 A1 | 2/2008 | To et al. |
| 2008/0051832 A1 | 2/2008 | To et al. |
| 2008/0051837 A1 | 2/2008 | To et al. |
| 2008/0058868 A1 | 3/2008 | To et al. |
| 2008/0234728 A1 | 9/2008 | Starksen et al. |
| 2008/0294177 A1 | 11/2008 | To et al. |
| 2009/0182417 A1 | 7/2009 | Tremulis et al. |
| 2009/0222083 A1 | 9/2009 | Nguyen et al. |
| 2009/0276038 A1 | 11/2009 | Tremulis et al. |
| 2010/0049213 A1 | 2/2010 | Serina et al. |

| | | | |
|---|---|---|---|
| 2010/0082098 A1 | 4/2010 | Starksen et al. | |
| 2010/0094314 A1 | 4/2010 | Hernlund et al. | |
| 2010/0121349 A1 | 5/2010 | Meier et al. | |

FOREIGN PATENT DOCUMENTS

| | | |
|---|---|---|
| JP | 6-510460 A | 11/1994 |
| JP | 11-506628 A | 6/1999 |
| WO | WO-93/08740 A1 | 5/1993 |
| WO | WO-94/03227 A1 | 2/1994 |
| WO | WO-95/15715 A1 | 6/1995 |
| WO | WO-96/08208 A1 | 3/1996 |
| WO | WO-96/39081 A1 | 12/1996 |
| WO | WO-96/39942 A1 | 12/1996 |
| WO | WO-97/27799 A1 | 8/1997 |
| WO | WO-97/27807 A1 | 8/1997 |
| WO | WO-97/30639 A1 | 8/1997 |
| WO | WO-98/07375 A1 | 2/1998 |
| WO | WO-00/60995 A2 | 10/2000 |
| WO | WO-00/60995 A3 | 10/2000 |
| WO | WO-00/67640 A2 | 11/2000 |
| WO | WO-00/67640 A3 | 11/2000 |
| WO | WO-01/26586 A1 | 4/2001 |
| WO | WO-01/54618 A1 | 8/2001 |
| WO | WO-02/03892 A1 | 1/2002 |
| WO | WO-02/051329 A1 | 7/2002 |
| WO | WO-02/085251 A1 | 10/2002 |
| WO | WO-02/085252 A1 | 10/2002 |
| WO | WO-03/088875 A1 | 10/2003 |
| WO | WO-03/105667 A2 | 12/2003 |
| WO | WO-03/105667 A3 | 12/2003 |
| WO | WO-03/105670 A2 | 12/2003 |
| WO | WO-03/105670 A3 | 12/2003 |
| WO | WO-2004/037317 A2 | 5/2004 |
| WO | WO-2004/037317 A3 | 5/2004 |
| WO | WO-2004/082523 A2 | 9/2004 |
| WO | WO-2004/082523 A3 | 9/2004 |
| WO | WO-2004/082538 A2 | 9/2004 |
| WO | WO-2004/082538 A3 | 9/2004 |
| WO | WO-2005/025644 A2 | 3/2005 |
| WO | WO-2005/025644 A3 | 3/2005 |
| WO | WO-2005/062931 A2 | 7/2005 |
| WO | WO-2005/062931 A3 | 7/2005 |
| WO | WO-2005/102181 A1 | 11/2005 |
| WO | WO-2006/034243 A2 | 3/2006 |
| WO | WO-2006/034243 A3 | 3/2006 |
| WO | WO-2006/037073 A2 | 4/2006 |
| WO | WO-2006/097931 A2 | 9/2006 |
| WO | WO-2006/097931 A3 | 9/2006 |
| WO | WO-2006/116558 A2 | 11/2006 |
| WO | WO-2006/116558 A3 | 11/2006 |
| WO | WO-2006/116558 C2 | 11/2006 |
| WO | WO-2007/001936 A2 | 1/2007 |
| WO | WO-2007/001936 A3 | 1/2007 |
| WO | WO-2007/005495 A1 | 1/2007 |
| WO | WO-2007/021564 A1 | 2/2007 |
| WO | WO-2007/021834 A1 | 2/2007 |
| WO | WO-2007/035449 A2 | 3/2007 |
| WO | WO-2007/056502 A1 | 5/2007 |
| WO | WO-2007/100409 A2 | 9/2007 |
| WO | WO-2008/028135 A2 | 3/2008 |
| WO | WO-2008/028135 A3 | 3/2008 |

OTHER PUBLICATIONS

Supplementary European Search Report mailed on Nov. 10, 2008, for EP Application No. 04 78 2847, filed on Sep. 1, 2004, 2 pages.
U.S. Appl. No. 12/187,331, filed Aug. 6, 2008, by To et al.
U.S. Appl. No. 12/581,040, filed Oct. 16, 2009, by Starksen et al.
De Simone, R. et al. (Apr. 15, 1993). "Adjustable Tricuspid Valve Annuloplasty Assisted by Intraoperative Transesophageal Color Doppler Echocardiography," *Am. J. Cardiol.* 71(11):926-931.
De Simone, R. et al. (Apr. 1, 1994). "Adjustable Annuloplasty for Tricuspid Insufficiency with External Control," *Reader's Comments and Reply, Am. J. Cardiol.* 73(9):721-722.
Downing, S.W. et al. (2002). "Feasibility of Off-Pump ASD Closure Using Real-Time 3-D Echocardiography," *The Heart Surgery Forum* 5(2):96-99, Abstract 7025.
International Search Report mailed Dec. 19, 2006, for PCT Application No. PCT/US2006/031190, filed Aug. 10, 2006, four pages.
International Search Report mailed on Apr. 2, 2007, for PCT Application No. PCT/US2006/043597, filed Nov. 8, 2006, seven pages.
Nagy, Z.L. et al. (Dec. 2000). "Mitral Annuloplasty with a Suture Technique," *European Journal of Cardio-thoracic Surgery* 18(6):739-740.
Shumway, S.J. et al. (Dec. 1988). "A 'Designer' Annuloplasty Ring for Patients with Massive Mitral Annular Dilatation," *Ann. Thorac. Surg.* 46(6):695-696.
U.S. Appl. No. 11/656,141, filed Jan. 19, 2007, by Straksen et al.
U.S. Appl. No. 11/875,774, filed Oct. 19, 2007, by Serina et al.
U.S. Appl. No. 12/132,161, filed Jun. 3, 2008, by Starksen et al.
U.S. Appl. No. 12/850,531, filed on Aug. 4, 2010, by Starksen et al.

DEVICES AND METHODS FOR CARDIAC ANNULUS STABILIZATION AND TREATMENT

CROSS REFERENCE TO RELATED APPLICATIONS

The present application is a divisional of U.S. application Ser. No. 10/656,797, filed Sep. 4, 2003, which is related to, and contains subject matter in common with, U.S. patent application Ser. No. 10/461,043, filed on Jun. 13, 2003, which is assigned to the assignees of the present invention, and which is hereby incorporated fully by reference.

BACKGROUND OF THE INVENTION

1. Field of the Invention

The present invention relates generally to medical devices and methods. More particularly, the invention relates to devices and methods for enhancing cardiovascular valve repair, especially the repair of heart valves such as the mitral and tricuspid valves.

In recent years, many advances have been made to reduce the invasiveness of cardiac surgery. In an attempt to avoid open, stopped-heart procedures, which may be accompanied by high patient morbidity and mortality, many devices and methods have been developed for operating on a heart through smaller incisions, operating on a beating heart, and even performing cardiac procedures via transvascular access. Different types of cardiac procedures, such as cardiac ablation techniques for treating atrial fibrillation, stenting procedures for atherosclerosis, and valve repair procedures for treating conditions such as mitral valve regurgitation have experienced significant technological advances. In implementing many minimally invasive cardiac surgery techniques, especially beating-heart techniques, one of the most significant challenges is exposing and stabilizing a portion of cardiac tissue to be operated upon. Another challenge, once exposure and stability are achieved, is to effectively deploy a given treatment into or on the target cardiac tissue using minimally invasive devices.

One type of cardiac surgery which may benefit from less invasive techniques is heart valve repair. Traditional treatment of heart valve stenosis or regurgitation, such as mitral or tricuspid regurgitation, typically involves an open-heart surgical procedure to replace or repair the valve. Valve repair procedures typically involve annuloplasty, a set of techniques designed to restore the valve annulus shape and strengthen the annulus. Conventional annuloplasty surgery generally requires a large incision into the thorax of the patient (a thoracotomy), and sometimes a median sternotomy (cutting through the middle of the sternum). These open heart, open chest procedures routinely involve placing the patient on a cardiopulmonary bypass machine for sustained periods so that the patient's heart and lungs can be artificially stopped during the procedure. Finally, valve repair and replacement procedures are typically technically challenging and require a relatively large incision through the wall of the heart to access the valve.

Due to the highly invasive nature of open heart valve repair or replacement, many patients, such as elderly patients, patients having recently undergone other surgical procedures, patients with comorbid medical conditions, children, late-stage heart failure patients, and the like, are often considered too high-risk to undergo heart valve surgery and are relegated to progressive deterioration and cardiac enlargement. Often, such patients have no feasible alternative treatments for their heart valve conditions.

To obviate this situation, a number of devices and methods for repairing cardiac valves in a less invasive manner have been described. Some devices provide for heart valve repair through minimally invasive incisions or intravascularly, while others improve upon open heart surgical procedures on beating hearts, stopped hearts or both. For example, several improved devices and methods for heart valve repair are described in one or more patent applications filed by the inventors of the present invention and assigned to the assignee of the present invention. For further description of such devices and methods, reference may be made to U.S. patent application Ser. No. 10/461043, filed on Jun. 13, 2003, previously incorporated by reference.

As mentioned above, some of the difficulties in performing minimally invasive intracardiac surgery include exposing and stabilizing an area of cardiac tissue to be operated upon and effectively operating on that tissue using minimally invasive instruments. Sufficient exposure is essential for allowing the physician to locate and perform a procedure on the targeted cardiac tissue. Stabilization further facilitates an intracardiac procedure, especially in a beating heart. In minimally invasive, beating heart surgery on a cardiac valve annulus, exposure and stabilization are especially challenging, due to rapid movement of the annulus and the heart, the small size of the annulus, and the blood-filled surgical field. While a cardiac valve may be visualized via transesophageal echocardiogram (TEE), it is much more difficult to locate the annulus itself, as it is basically a small band of fibrous tissue. Exposure of the annulus is essential, however, since annular tissue is far stronger than surrounding valve leaflet and heart wall tissue, and repair procedures performed on a valve annulus will be much more effective than those performed on other tissue adjacent the annulus. Even after a valve annulus is exposed and stabilized, it may still be challenging to effectively and efficiently operate on the annulus to repair the valve, using minimally invasive devices.

Many minimally invasive or "less invasive" surgical procedures other than heart valve repair would also benefit from improved exposure and/or stabilization. For example, improved exposure and stabilization could facilitate other cardiac procedures, such as accessing the coronary sinus for placement of an implantable device or for performing a procedure, placing pacemaker leads in one or more areas of the heart, ablation procedures such as ablation around the pulmonary veins to treat atrial fibrillation, atrial-septal defect repair procedures, and the like. Improved stabilization and exposure could also be used to enhance non-cardiac procedures such as cinching or otherwise treating a bladder, stomach, gastroesophageal junction, vascular structure, gall bladder or the like.

Therefore, it would be beneficial to have devices and methods for enhancing exposure and/or stabilization in transvascular, minimally invasive and other "less invasive" surgical procedures, such as heart valve repair and other cardiac procedures. Ideally, for example, such devices and method could be used for exposing and stabilizing a cardiac valve annulus for performing a valve repair procedure. Ideally, such devices and methods could be used in minimally invasive or "less invasive" beating heart procedures performed via a variety of access routes, such as transvascular or transthoracic. Also ideally, some devices might be used for exposing a valve annulus, others might expose and stabilize an annulus, and still others might expose, stabilize and administer a therapy to an annulus, thus providing a physician with numerous procedural options. At least some of these objectives will be met by the present invention.

2. Description of the Background Art

Published U.S. Application 2002/0156526 describes a catheter-based method for performing annuloplasty. Published U.S. Application 2002/0042621 describes a heart valve annuloplasty system with constrictable plication bands which are optionally attached to a linkage strip. Published U.S. Application 2002/0087169 describes a remote controlled catheter system which can be used to deliver anchors and a tether for performing an annuloplasty procedure. Other patent publications of interest include WO01/26586; US2001/0005787; US2001/0014800; US2002/0013621; US2002/0029080; US2002/0035361; US2002/0042621; US2002/0095167; and US2003/0074012. U.S. patents of interest include U.S. Pat. Nos. 4,014,492; 4,042,979; 4,043,504; 4,055,861; 4,700,250; 5,366,479; 5,450,860; 5,571,215; 5,674,279; 5,709,695; 5,752,518; 5,848,969;5,860,992; 5,904,651; 5,961,539; 5,972,004; 6,165,183; 6,197,017; 6,250,308; 6,260,552; 6,283,993; 6,269,819; 6,312,447; 6,332,893; and 6,524,338. Publications of interest include De Simone et al. (1993) *Am. J. Cardiol.* 73:721-722, and Downing et al. (2001) *Heart Surgery Forum*, Abstract 7025.

BRIEF SUMMARY OF THE INVENTION

Devices and methods of the present invention are generally used to facilitate transvascular, minimally invasive and other "less invasive" surgical procedures, by enhancing exposure, stabilization and/or the like of a tissue or structure upon which a procedure is to be performed. "Less invasive," for the purposes of this application, means any procedure that is less invasive than traditional, large-incision open surgical procedures. Thus, a less invasive procedure may be an open surgical procedure involving one or more relatively small incisions, a transvascular percutaneous procedure, a transvascular procedure via cut-down, a laparoscopic or other endoscopic procedure, or the like. Generally, any procedure in which a goal is to minimize or reduce invasiveness to the patient may be considered less invasive. Furthermore, although the terms "less invasive" and "minimally invasive" may sometimes be used interchangeably in this application, neither these nor terms used to describe a particular subset of surgical or other procedures should be interpreted to limit the scope of the invention. Generally, stabilization/exposure devices and methods of the invention may be used in performing or enhancing any suitable procedure.

As mentioned above, the present application typically describes devices and methods for stabilization and/or exposure in the context of heart valve repair, and more specifically mitral valve repair to treat mitral regurgitation. It should be emphasized, however, that devices and methods of the invention may be used in any suitable procedure, both cardiac and non-cardiac. For example, they may be used in procedures to repair any heart valve, to repair an atrial-septal defect, to access and possibly perform a procedure from (or through) the coronary sinus, to place one or more pacemaker leads, to perform a cardiac ablation procedure such as ablating around pulmonary veins to treat atrial fibrillation, and/or the like. In other embodiments, the devices and methods may be used to enhance a laparoscopic or other endoscopic procedure on any part of the body, such as the bladder, stomach, gastroesophageal junction, vasculature, gall bladder, or the like. Therefore, although the following description typically focuses on mitral valve and other heart valve repair, such description should not be interpreted to limit the scope of the invention as defined by the claims.

That being said, the present invention generally provides devices and methods for enhanced stabilization, exposure and/or treatment of a cardiac valve annulus. Methods generally involve introducing a stabilizing member beneath one or more leaflets of a heart valve to engage the ventricular side of the annulus at an intersection between the leaflets and the interior ventricular wall of the heart. The stabilizing member will usually be curved or C-shaped to conform to at least a portion of the ventricular side of the annulus, and force is applied to the stabilizing member to engage and stabilize the valve annulus. By "stabilize," it is meant that the annulus will be at least partially immobilized relative to the cardiac tissue surrounding the annulus, at least partially delineated or exposed relative to cardiac tissue surrounding the annulus, or both. For example, in some instances "stabilization" may not involve immobilizing annular tissue but may instead involve moving or positioning annular tissue in such a way to allow enhanced visualization of that tissue relative to surrounding tissues.

As just mentioned, in addition to stabilizing, methods and apparatus of the present invention may also help expose, position, or delineate the valve annulus, to enhance the physician's ability to view and operate on the annular tissue. Some embodiments also include a second stabilizing member, to be introduced above the leaflets, allowing a physician to grasp or clamp annular tissue between the upper and lower stabilizing members for further stabilization. Various embodiments further provide for treatment of a valve annulus. For example, either the upper or lower stabilizing member may include actuators or effectors for performing any one or more of a variety of interventions. For example, either or both stabilizing members may be adapted to deliver devices for constricting or reshaping the valve annulus to treat regurgitation or other conditions. The devices may comprise anchors, tethered anchors, rings, or the like for reinforcing or cinching the annulus. In a specific example, the stabilizing member may be configured to hydraulically or otherwise deliver a series of tethered hooks, tethered clips or other tethered anchors or fasteners for engaging and cinching valve annulus tissue to decrease the diameter of a regurgitant valve. The stabilizer(s) will also be adaptable for delivering other therapies, including applying radiofrequency energy (or other heat sources) to shrink the collagen tissue in the annulus, delivering bulking agents, delivering drugs and biological agents such as growth factors, delivering agents for providing cell dedifferentiation, and/or the like.

In most cases, the methods of the present invention will be performed on a beating heart. Access to the beating heart may be accomplished by any available technique, including intravascular, transthoracic, and the like. In addition to beating heart access, the methods of the present invention may be used for intravascular stopped heart access as well as stopped heart open chest procedures.

In one aspect of the invention, a method for stabilizing a valve annulus of a heart for performing a procedure on the valve annulus involves first introducing at least a first stabilizing member beneath one or more leaflets of a valve of the heart to engage an intersection between at least one leaflet and the interior ventricular wall of the heart. Force is then applied to the first stabilizing member to stabilize the valve annulus. Usually, the stabilizing member engages the ventricular annulus (in the case of a mitral valve), and applying force comprises drawing the stabilizing member upwardly against the annulus to immobilize the annular tissue relative to the surrounding tissue. When a second stabilizing member is employed, applying force comprises applying opposed forces with the "upper and lower" stabilizing members to further stabilize the annular tissue. Such methods may be used on any of a number of cardiac or circulatory valves or other body structures such as valves in body lumens, but in one embodiment, for example, the first stabilizing member is passed beneath the posterior leaflet of the mitral valve. In addition to stabilizing the annular tissue, applying pressure with the stabilization device may also expose the valve annulus from surrounding tissue of the heart, for improved visualization and access by the physician.

In some embodiments, introducing the device comprises advancing a flexible, elongate catheter through vasculature of a patient to the heart, with at least a first stabilizing member comprising a shape-changing member at a distal end of the flexible elongate catheter. The catheter may be introduced through the vasculature with the shape-changing stabilizing member in a generally straight, flexible configuration. Once it is in place beneath the leaflet at the intersection between the leaflet and the interior ventricular wall, the shape of the stabilizing member is changed to conform to the annulus and usually the shape is "locked" to provide sufficient stiffness or rigidity to permit the application of force from the stabilizing member to the annulus. Shaping and optionally locking the stabilizing member may be accomplished in any of a number of ways, such as applying tension to tensioning cord(s), as described in detail below.

In transthoracic and other embodiments, the stabilizing member may be pre-shaped, and the method may simply involve introducing the stabilizing member(s) under and/or over the valve leaflets. The pre-shaped stabilizing member(s) may be rigid or formed from a shape memory material such as nitinol, spring stainless steel, or the like.

Force applied to the first stabilizing member is often upwardly directed, though lateral forces are also possible. In addition to stabilizing with force from below the annulus, stabilizing may optionally include introducing a second stabilizing member over the valve leaflets. By moving the second stabilizing member toward the first stabilizing member, a physician may grip or clamp all or a portion of the valve annulus.

In another aspect, a method for performing a procedure on a stabilized valve annulus includes advancing a flexible, elongate stabilizing catheter through vasculature of a patient to the heart. Next, a shape-changing stabilizing member on the catheter is positioned beneath one or more leaflets of a valve of the heart to engage the lower or ventricular annulus at an intersection between at least one leaflet and an interior ventricular wall of the heart. The shape of the stabilizing member is then changed and optionally locked to conform to the annulus, and an upward and/or other force is applied to the stabilizing member to stabilize the valve annulus.

In still another aspect of the present invention, a method for constricting a valve annulus in a beating heart comprises introducing at least a first stabilizing member beneath one or more leaflets of a valve of the heart to engage the annulus at an intersection between at least one leaflet and an interior ventricular wall of the heart. Force is then applied to the first stabilizing member to stabilize the valve annulus. A plurality of individual anchors, such as hooks, clips, barbs, T-tags, rings, anchors made of resorbable polymers such as polylactic acid or polyglycolic acid, or the like, may then be placed at circumferentially spaced-apart locations about at least a portion of the valve annulus while the valve annulus remains stabilized. The anchors may then be cinched via a tether to circumferentially tighten the annulus. Optionally, the method may further include introducing at least a second stabilizing member over the valve leaflets and moving the second stabilizing member toward the first stabilizing member to further stabilize the annulus. In some embodiments, securing the anchors comprises driving the anchors from one of the first and second stabilizing members. Driving the anchors, in turn, may involve inflating an expandable balloon in one of the members to force the anchors at least partially out of the member into tissue of the valve annulus. Optionally, securing the anchors may also involve driving the anchors through tissue of the valve annulus into a anchor receiving piece coupled with the other stabilizing member.

Throughout the present application, the term "anchor" is frequently used to a device for coupling with a valve annulus or other bodily structure. For the purposes of this application, "anchor" means any fastener or other attachment device. Thus, an anchor may be a hook, such as a curved hook or a straight, barbed hook, a clip, a T-tag, a ring, an adhesive strip, a shape-memory fastening device or any other fastener. Furthermore, anchors may be made of any suitable material. For example, an anchor may be made of a metal, such as stainless steel, or may alternatively be made of a bioresorbable material such as polylactate or polyglycolate, such that over time, after a body structure has repaired, the anchors may be resorbed. Therefore, although various examples of anchors are described below and various terms such as "hooks" may be used to describe fastening devices of the invention, these terms should not be interpreted to limit the scope of the invention as defined by the claims.

In yet another aspect of the invention, a device for enhancing a surgical procedure on a valve annulus of a heart includes an elongate body having a proximal end and a distal end and at least a first stabilizing member at the distal end of the shaft. Generally, the first stabilizing member is passable under one or more leaflets of a valve of the heart to engage an intersection between at least one leaflet and an interior ventricular wall of the heart. In some embodiments, the elongate body comprises a rigid shaft. In alternative embodiments, the elongate body comprises a flexible catheter, so that the first stabilizing member may be passed into the heart and under the one or more leaflets via a transvascular approach.

The first stabilizing member may comprise a shape-changing portion. By "shape-changing," it is meant that at least a segment of the stabilizing member may be transitioned between (a) a straight or flexible configuration (to facilitate introduction) and (b) a fixed-shape configuration, generally a curved or C-shaped segment which conforms to the shape of the valve annulus. Such shape-changing may be accomplished by a variety of mechanical approaches. In some embodiments, for example, the first stabilizing member may include a slotted, segmented or sectioned tube coupled with one or more pull cords. Tension may be applied to one pull cord to bend the segmented tube into a C-shape, while tension may be applied to the other cord to bend the tube up, or proximally. Generally, a segmented tube and two pull cords can be used to shape a stabilizing member around two bends having any desired configuration. In another embodiment, a shape-memory material may be included in the first stabilizing member, and introducing fluid into the member may cause it to change from a straight configuration to a C-shape. In some embodiments, the shape-changing portion may be locked in position to enhance stabilization of the annulus.

In some embodiments, the first stabilizing member includes a semicircular housing, a plurality of tethered anchors disposed within the housing, and at least one expandable balloon for driving the plurality of anchors into tissue of the valve annulus. In some embodiments, the device may include an inflation actuator for inflating the expandable balloon, a release actuator for releasing the anchors from the housing, and a cinching actuator for cinching a tether coupled with the tethered anchors to reduce a diameter of the valve annulus. The first stabilizing member may be configured to allowing driving of the plurality of anchors in any suitable direction or configuration. For example, in some embodiments the first stabilizing member will be configured for positioning under a heart valve annulus and for driving anchors upwards (or superiorly) into or through the annulus. In another embodiment, a stabilizing member may be configured for positioning above an annulus and for driving anchors downwards. Alternatively, a stabilizing member may be positioned outside a heart wall or other structure, with anchors driven inwardly. And as discussed above, these devices may be used to perform other cardiac and non-cardiac procedures, such as anchoring and cinching a gastroesophageal junction, bladder outlet or other structure.

As mentioned above, some embodiments also include at least a second stabilizing member movably coupled with the elongate shaft, wherein the second stabilizing member may be moved toward the first stabilizing member to grip and stabilize the valve annulus. Optionally, such embodiments may also include one or more anchor receiving pieces coupled with the second stabilizing member for receiving distal ends of the plurality of anchors driven through the tissue of the valve annulus. In some embodiments, each of the first and second stabilizing members comprises a flexible rigidifying portion. Alternatively, each of the first and second stabilizing members may comprise a rigid member. Some embodiments may also include a handle near the proximal end of the shaft for moving the second stabilizing member toward the first stabilizing member to grip the valve annulus.

In alternative embodiments, either the first stabilizing member, the second stabilizing member or both may include any of a number of annulus treatment devices. For example, in one embodiment a stabilizing member may include an energy deliver device, such as a radiofrequency delivery device, for transmitting energy to a valve annulus to constrict the annular tissue. In another embodiment, a stabilizing member may include a mechanical support member or other deployable device that is couplable with a valve annulus. For example, a shape memory stent may be coupled with a stabilizing member such that when the stent is coupled with annular tissue and deployed, it shrinks longitudinally to reduce the diameter of the annulus. In other embodiments, multiple such stents may be used. These and other embodiments are described more fully below with reference to the drawing figures.

DETAILED DESCRIPTION OF THE INVENTION

Figure 1:
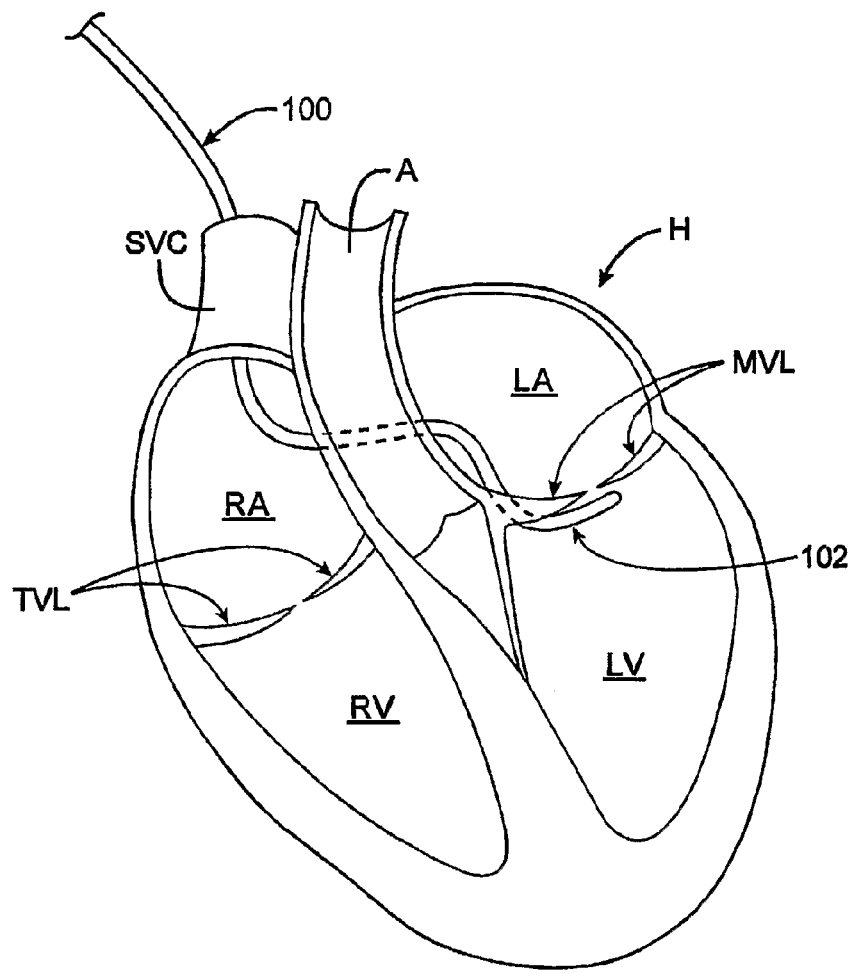
FIG. 1 is a cross-sectional view of a heart with a flexible stabilization device being positioned for stabilizing a valve annulus, according to one embodiment of the present invention.

Devices and methods of the present invention are generally used to facilitate transvascular, minimally invasive and other "less invasive" surgical procedures, by enhancing exposure, stabilization and/or the like of a tissue or structure upon which a procedure is to be performed. As discussed more fully above, "less invasive," for the purposes of this application, means any procedure that is less invasive than traditional, large-incision open surgical procedures. Thus, a less invasive procedure may be an open surgical procedure involving one or more relatively small incisions, a transvascular percutaneous procedure, a transvascular procedure via cut-down, a laparoscopic or other endoscopic procedure, or any procedure in which a goal is to minimize or reduce invasiveness to the patient may be considered less invasive.

The present application typically describes devices and methods for stabilization and/or exposure in the context of heart valve repair, and more specifically mitral valve repair to treat mitral regurgitation. Devices and methods of the invention may be used in any suitable procedure, however, both cardiac and non-cardiac. For example, they may be used in procedures to repair any heart valve, to repair an atrial-septal defect, to access and possibly perform a procedure from (or through) the coronary sinus, to place one or more pacemaker leads, to perform a cardiac ablation procedure such as ablating around pulmonary veins to treat atrial fibrillation, and/or the like. In other embodiments, the devices and methods may be used to enhance a laparoscopic or other endoscopic procedure on any part of the body, such as the bladder, stomach, gastroesophageal junction, vasculature, gall bladder, or the like. In some embodiments, for example, devices and methods include coupling multiple tethered anchors to a valve annulus and cinching the annulus to reduce a diameter of the valve. Similar devices and methods may be used, alternatively, to close or reduce the diameter of an atrial-septal defect, a gastroesophageal junction, or any other suitable body lumen, valve or other structure. Therefore, although the following description typically focuses on mitral valve and other heart valve repair, such description should not be interpreted to limit the scope of the invention as defined by the claims.

Devices and methods of the invention generally provide for enhanced stabilization, exposure and/or treatment of a cardiac valve annulus. By "stabilize," it is meant that the annulus will be at least partially immobilized relative to the cardiac tissue surrounding the annulus, at least partially delineated or exposed relative to cardiac tissue surrounding the annulus, or both. For example, in some instances "stabilization" may not involve immobilizing annular tissue but may instead involve moving or positioning annular tissue in such a way to allow enhanced visualization of that tissue relative to surrounding tissues. Methods generally involve introducing a stabilizing member beneath one or more leaflets of a heart valve to engage the ventricular side of the annulus at an intersection between the leaflets and the interior ventricular wall of the heart. The stabilizing member will usually be curved or C-shaped to conform to at least a portion of the ventricular side of the annulus, and force is applied to the stabilizing member to engage and stabilize the valve annulus.

In addition to stabilizing, methods and apparatus of the present invention may also help expose, position, or delineate the valve annulus, to enhance the physician's ability to view and operate on the annular tissue. Some embodiments also include a second stabilizing member, to be introduced above the leaflets, allowing a physician to grasp or clamp annular tissue between the upper and lower stabilizing members for further stabilization. Various embodiments further provide for treatment of a valve annulus. For example, either the upper or lower stabilizing member may include actuators or effectors for performing any one or more of a variety of interventions. For example, either or both stabilizing members hay be adapted to deliver devices for constricting or reshaping the valve annulus to treat regurgitation or other conditions. The devices may comprise anchors, tethered anchors, rings, or the like for reinforcing or cinching the annulus. In a specific example, the stabilizing member may be configured to hydraulically or otherwise deliver a series of tethered hooks, tethered clips or other tethered anchors or fasteners for engaging and cinching valve annulus tissue to decrease the diameter of a regurgitant valve. The stabilizer(s) will also be adaptable for delivering other therapies, including applying radiofrequency energy (or other heat sources) to shrink the collagen tissue in the annulus, delivering bulking agents, delivering drugs and biological agents such as growth factors.

In most cases, the methods of the present invention will be performed on a beating heart. Access to the beating heart may be accomplished by any available technique, including intravascular, transthoracic, and the like. In addition to beating heart access, the methods of the present invention may be used for intravascular stopped heart access as well as stopped heart open chest procedures.

Referring now to FIG. 1, a heart H is shown in cross section, with a stabilization device 100 introduced within the heart H. Generally, stabilization device 100 comprises an elongate body with at least a first stabilizing member 102 at its distal end for providing stabilization and/or exposure of a heart valve annulus. In some embodiments, the elongate body comprises a rigid shaft, while in other embodiments it comprises a flexible catheter, so that the first stabilizing member may be positioned in the heart H and under one or more valve leaflets to engage an valve annulus via a transvascular approach. Transvascular access may be gained, for example, through the internal jugular vein (not shown) to the superior vena cava SVC to the right atrium RA, across the interatrial septum to the left atrium LA, and then under one or more mitral valve leaflets MVL to a position within the left ventricle (LV) under the valve annulus (not shown). Alternatively, access to the heart may be achieved via the femoral vein and the inferior vena cave In other embodiments, access may be gained via the coronary sinus (not shown) and through the atrial wall into the left atrium.

In other embodiments, access to the heart H may be transthoracic, with the stabilization device being introduced into the heart via an incision or port on the heart wall. Even open heart surgical procedures may benefit from methods and devices of the invention. Furthermore, some embodiments may be used to enhance procedures on the tricuspid valve annulus, adjacent the tricuspid valve leaflets TVL, or any other cardiac or vascular valve. Therefore, although the following description typically focuses on minimally invasive or less invasive mitral valve repair for treating mitral regurgitation, the invention is in no way limited to that use.

Figure 1A:
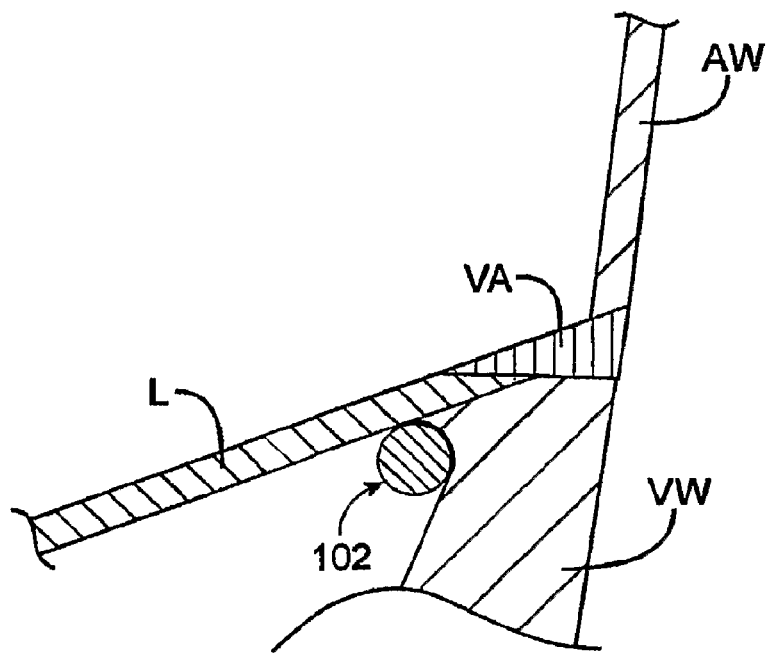
FIGS. 1A and 1B are cross-sectional views of a valve leaflet, valve annulus, atrial wall and ventricular wall, with a stabilization device in place for stabilizing and exposing the annulus, according to one embodiment of the present invention.
Figure 1B:
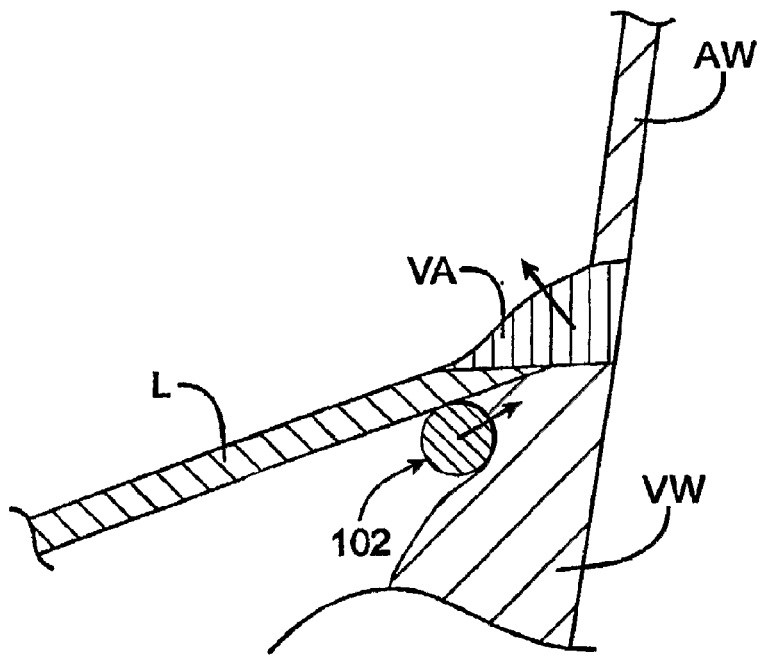

With reference to FIGS. 1A and 1B, a method for using stabilization device 100 is depicted in a cross-sectional view. First, as in FIG. 1A, stabilizing member 102 is positioned in a desired location under a valve leaflet L and adjacent a ventricular wall VW. The valve annulus generally comprises an area of heart wall tissue at the junction of the ventricular wall VW and the atrial wall AW that is relatively fibrous and, thus, significantly stronger that leaflet tissue and other heart wall tissue. Stabilizing member 102 may be advanced into position under the valve annulus by any suitable technique, some of which are described below in further detail. For example, using a stabilization device having a flexible elongate body as shown in FIG. 1, stabilizing member 102 may be passed from the right atrium RA through the interatrial septum in the area of the foramen ovale (not shown—behind the aorta A), into the left atrium LA. Oftentimes, stabilizing member 102 will then naturally travel, upon further advancement, under the posterior valve leaflet to a position under the valve annulus VA, as shown in FIG. 1A.

In some embodiments, stabilizing member 102 includes a shape-changing portion which enables stabilizing member 102 to conform to the shape of the valve annulus VA. The catheter may be introduced through the vasculature with the shape-changing stabilizing member in a generally straight, flexible configuration. Once it is in place beneath the leaflet at the intersection between the leaflet and the interior ventricular wall, the shape of stabilizing member 102 is changed to conform to the annulus and usually the shape is "locked" to provide sufficient stiffness or rigidity to permit the application of force from stabilizing member 102 to the annulus. Shaping and optionally locking stabilizing member 102 may be accomplished in any of a number of ways. For example, in some embodiments, a shape-changing portion may be sectioned, notched, slotted or segmented and one of more tensioning cords, wires or other tensioning devices coupled with the shape-changing portion may be used to shape and rigidify stabilizing member 102. A segmented stabilizing member, for example, may include multiple segments coupled with two tensioning cords, each cord providing a different direction of articulation to the stabilizing member. A first bend may be created by tensioning a first cord to give the stabilizing member a C-shape or similar shape to conform to the valve annulus, while a second bend may be created by tensioning a second cord to articulate the C-shaped member upwards against the annulus. In various embodiments, any configurations and combinations may be used to give stabilizing member 102 a desired shape.

In transthoracic and other embodiments, stabilizing member 102 may be pre-shaped, and the method may simply involve introducing stabilizing member 102 under the valve leaflets. The pre-shaped stabilizing member 102 may be rigid or formed from a shape memory material such as nitinol, spring stainless steel, or the like.

Once stabilizing member 102 is positioned under the annulus, force may be applied to stabilize the valve annulus VA, as shown in FIG. 1B. Such force may be directed in any suitable direction to expose, position and/or stabilize the annulus. For example, upward and lateral force is shown in FIG. 1B by the solid-headed arrow drawn from the center of stabilizing member 102. In other cases, only upward, only lateral, or any other suitable force(s) may be applied. With application of force to stabilizing member 102, the valve annulus VA is caused to rise or project outwardly, thus exposing the annulus for easier viewing and access. The applied force may also stabilize the valve annulus VA, also facilitating surgical procedures and visualization.

Figure 2:
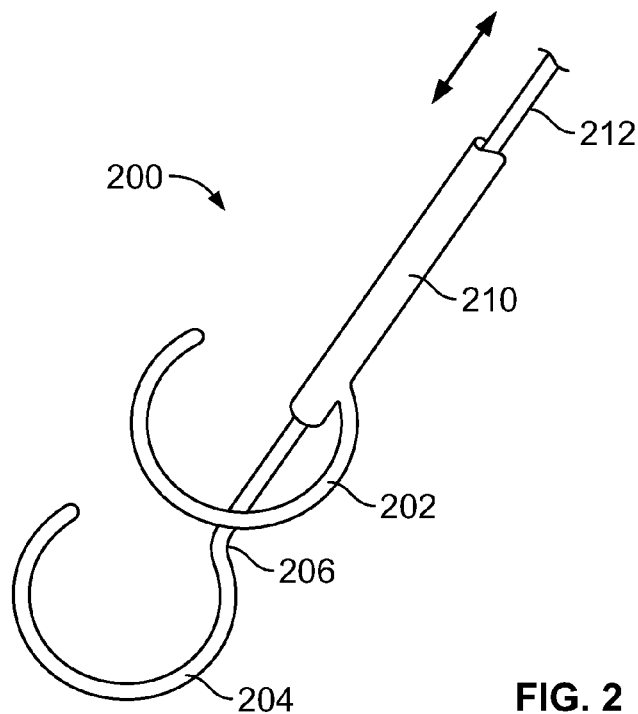
FIG. 2 is a perspective view of a stabilization device having two stabilization members, according to one embodiment of the present invention.

With reference now to FIG. 2, one embodiment of a stabilization device 200 may include an upper or atrial stabilizing member 202, coupled with an outer shaft 210, and a lower or ventricular stabilizing member 204 coupled with an inner shaft 212. Upper stabilizing member 202 and lower stabilizing member 204 are typically adapted for placement above and below a valve annulus, such as the mitral valve annulus. Stabilizing members 202 and 204 will typically be formed from an elastic material having a geometry selected to engage and optionally shape or constrict the valve annulus. For example, the rings may be formed from shape memory alloy, such as nitinol, from a spring stainless steel, or the like. In other instances, however, the stabilizing members could be formed from an inflatable or other structure can be selectively rigidified in situ, such as a gooseneck or lockable element shaft, any of the rigidifying structures described above, or any other rigidifying structure.

Figure 3:
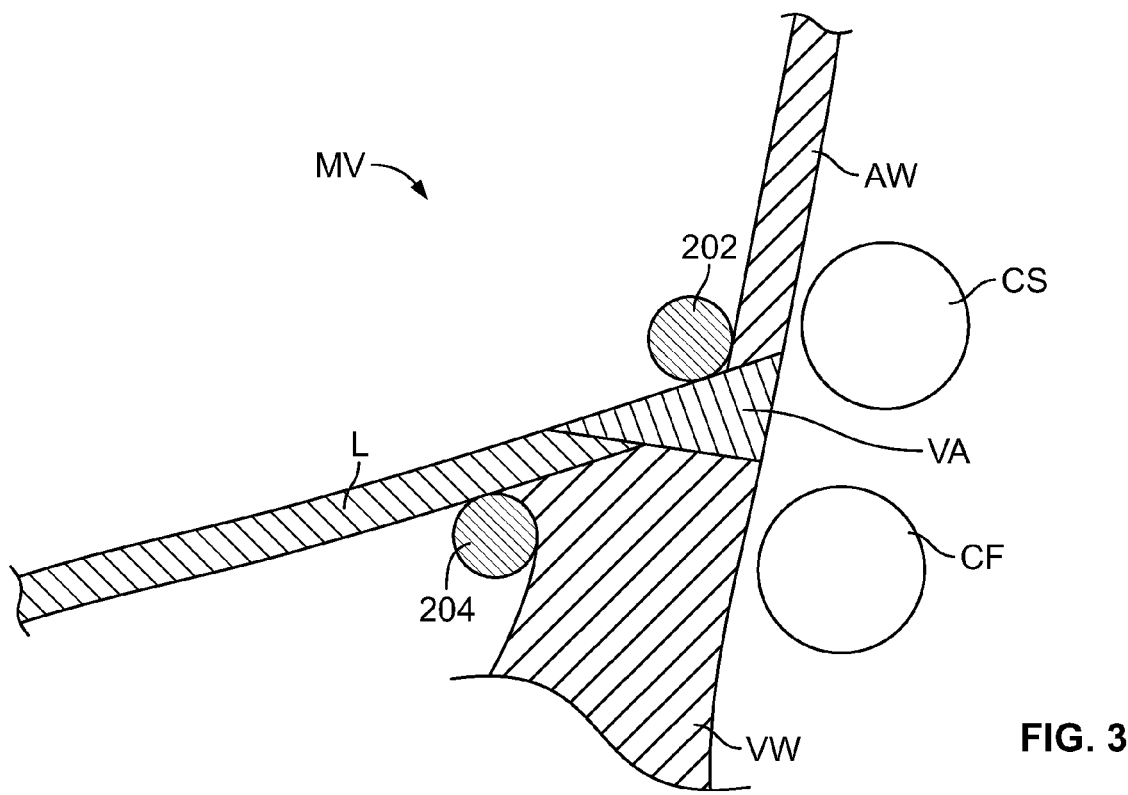
FIG. 3 is a cross-sectional view of a valve leaflet, valve annulus, atrial wall and ventricular wall, with a stabilization device in place having upper and lower stabilization members, according to one embodiment of the present invention.
Figure 4:
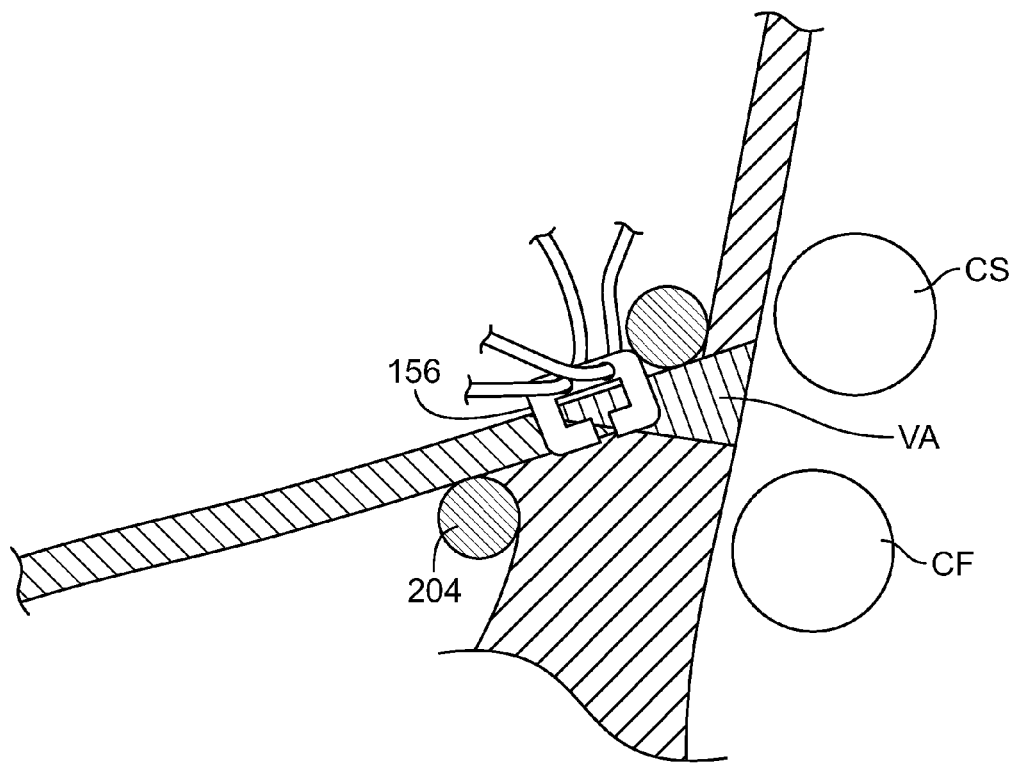
FIG. 4 shows a stabilization device as in FIG. 3 with a tethered clip placed in the valve annulus, according to one embodiment of the present invention.
Figure 5:
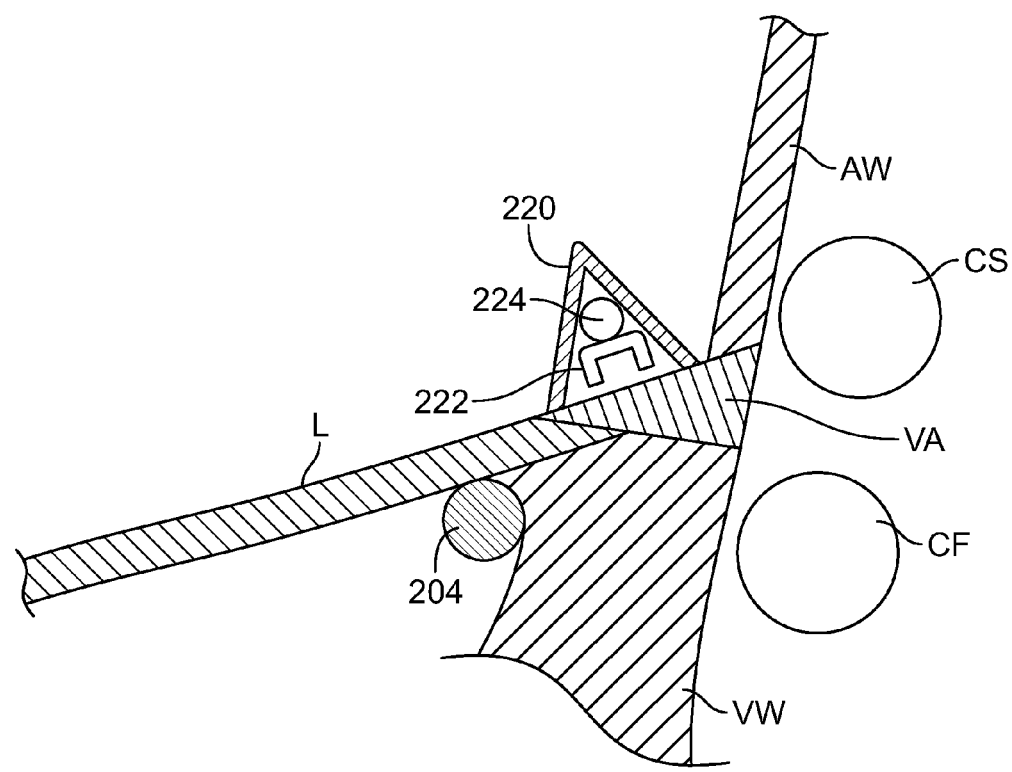
FIG. 5 shows a stabilization device having a balloon-driven clip applier as its upper stabilizing member, according to one embodiment of the present invention.

As described above, the device 200 may be introduced to the left atrium of a beating heart, either transeptally or through an incision in the heart wall. Once in the atrium, the lower or ventricular stabilizing member will be introduced through the mitral valve opening, with a corner 206 of the stabilizing member typically being engaged against a commisure. The ventricular stabilizing member 204 may be adjusted so that it lies at a junction between the valve leaflet L and the ventricular wall VW, as illustrated in FIG. 3. The upper or atrial stabilizing member 202 may then be clamped down onto the upper surface of the annulus VA, typically by sliding outer shaft 210 down over inner shaft 212. Thus, the annulus will be circumferentially clamped between the stabilizing members, again as observed in FIG.3. Such clamping will stabilize the annulus relative to the remainder of the beating heart, thus facilitating subsequent minimally invasive surgical procedures. For example, and with reference now to FIG. 4, a clip applier may be used to introduce individual tethered clips 156 into the valve annulus VA. Exemplary clip appliers for applying tethered clips to a valve annulus are described more fully in U.S. patent application Ser. No. 10/461043, which was previously incorporated by reference. Alternatively, atrial stabilizing member 202 could be replaced with a circular clip applier 220, as shown in FIG. 5. A stabilizing device employing such a clip applier could be used to simultaneously stabilize the annulus and deliver clips 222 using a clip driver, such as a balloon 224.

Although not illustrated, in some instances it may be desirable to provide a third stabilizing element on the exterior of the heart, optionally between the coronary sinus CS and circumflex artery CF or within the coronary sinus.

As is described further below, any stabilizing member, including an atrial stabilizing member, a ventricular stabilizing member, or both, may include one or more devices for treating a valve annulus. Such devices may include any suitable device for treating an annulus, and the present invention is not limited to any specific embodiments. For example, in some embodiments a stabilizing member comprises a housing for containing a plurality of tethered anchors and a system for delivering the anchors into annular tissue. "Anchors" may comprise curved hooks, straight hooks, barbed hooks, clips of any kind, T-tags, shape memory hooks, or any other suitable fastener(s). Delivery of anchors may be accomplished by any suitable device and technique, such as by hydraulic balloon delivery as discussed below. Alternatively, any other suitable treatment may be delivered to an annulus. For example, energy such as radiofrequency energy may be delivered to the annulus via a stabilizing member to constrict the annular tissue. Alternatively, a shape memory stent may be delivered to the annulus such that when deployed the stent longitudinally shrinks to constrict the annulus. In other embodiments, one or more drugs or bulking agents may be administered to the annulus. Therefore, although the following description focuses on delivery of a plurality of tethered hooks to a valve annulus, many other types of anchors and other treatment modalities may alternatively be delivered using devices and methods of the invention.

Figure 5A:
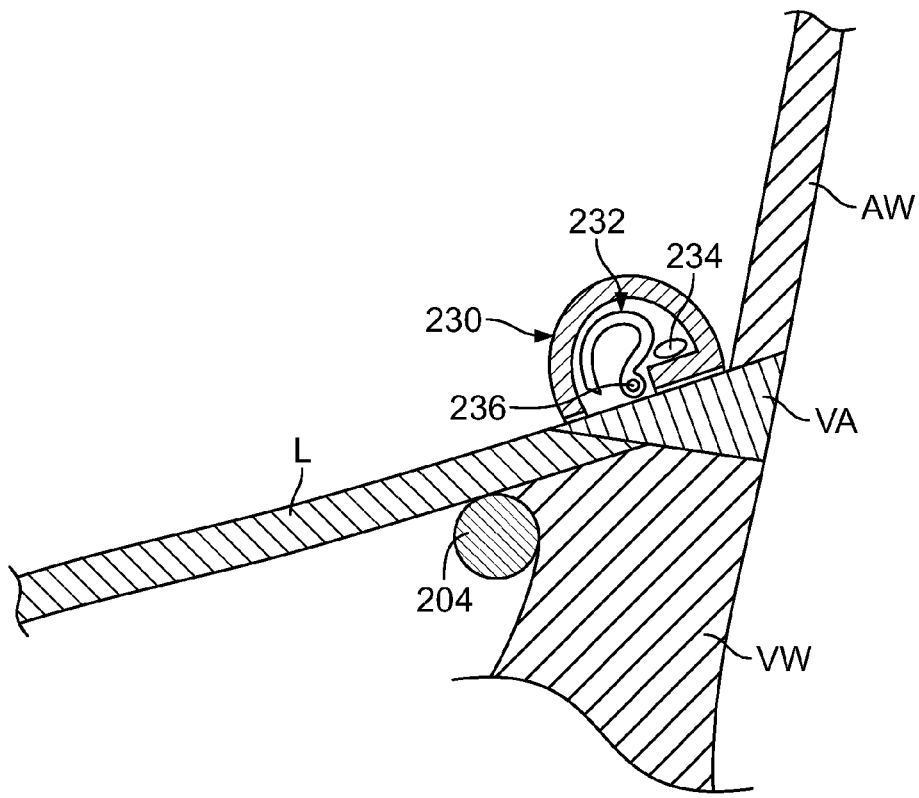
FIGS. 5A and 5B show a stabilization device having a balloon-driven hook applier as its upper stabilizing member, and a method for using same, according to one embodiment of the present invention.
Figure 5B:
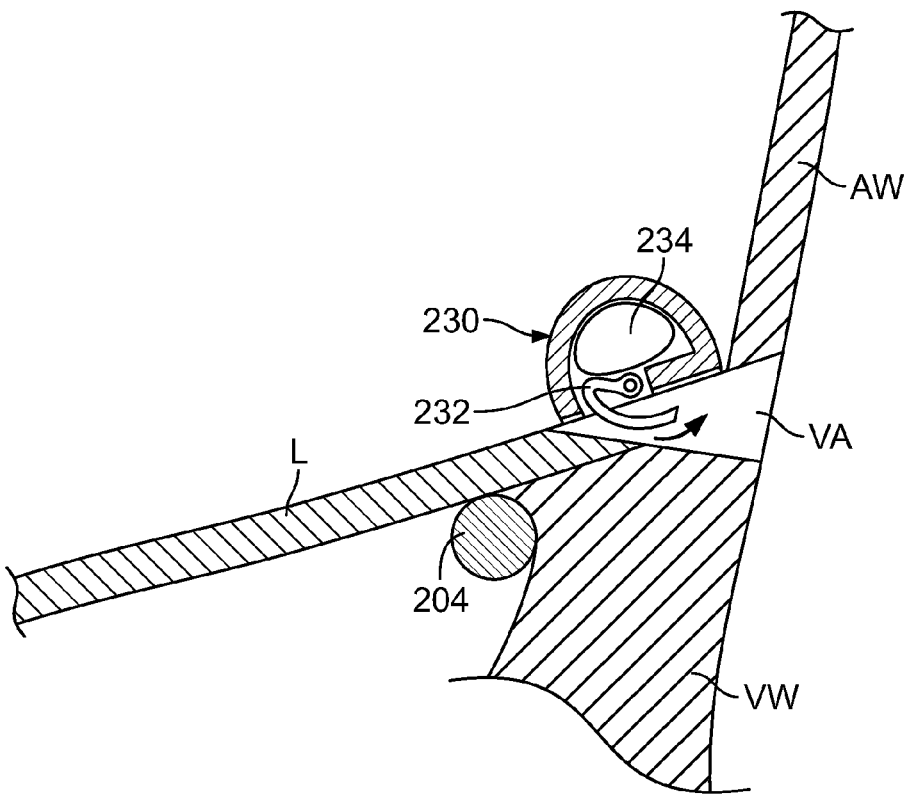

That being said, and referring now to FIGS. 5A and 5B, in one embodiment, upper stabilizing member 202 could be replaced with a circular hook applier 230, including a housing for multiple tethered hooks 232 and a hook driver such as a balloon 234. Again, hooks 232 may be replaced by any other anchors in various embodiments. Hooks 232 may be coupled to the device via a pivot mandrel 236, so that when balloon 234 is inflated, as in FIG. 5B, hooks 232 pivot around mandrel 236 to enter tissue of the valve annulus VA. Hydraulically driving curved hooks 232 in this way closely replicates the motion of a surgeon manually driving a suture needle into tissue and allows hooks 232 to be driven strongly into the tissue of the valve annulus VA. After hooks 232 are engaged with the valve annulus VA, they may be cinched, using the tether (not shown), to decrease the diameter of the annulus and thus the valve. The housing, the balloon 234 and the pivot mandrel 236 may be withdrawn before or after cinching.

As mentioned above, in various embodiments other anchor delivery mechanisms may be used, although one or more expandable balloons are used in one embodiment. For example, other hydraulic delivery systems may be used, anchors may be advanced into tissue using a pull-cord, or the like. In some embodiments, treatment devices and delivery mechanisms may be incorporated into lower/ventricular stabilizing member 204, rather than upper/atrial stabilizing member 202. In still other embodiments, some of which are described immediately below, both stabilizing members 202 and 204 may include devices for treatment of the valve annulus VA.

Figure 5C:
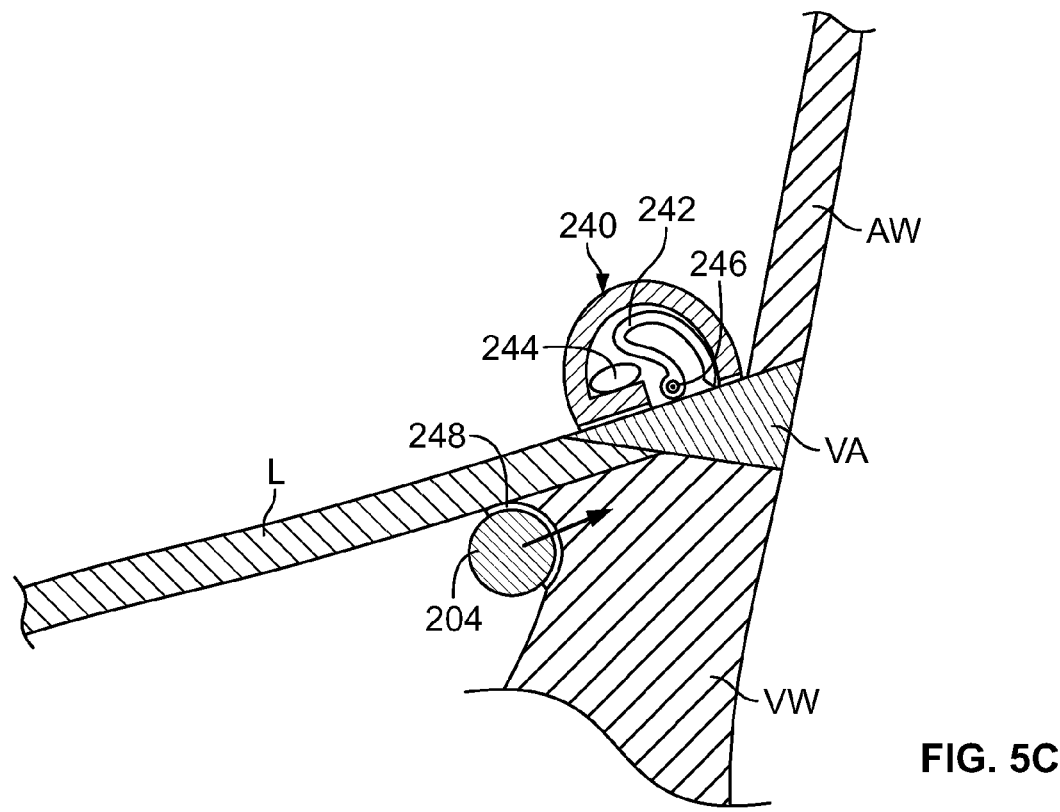
FIGS. 5C and 5D show a stabilization device having a balloon-driven hook applier as its upper stabilizing member, a lower stabilizing member carrying a hook receiver, and a method for using same, according to one embodiment of the present invention.
Figure 5D:
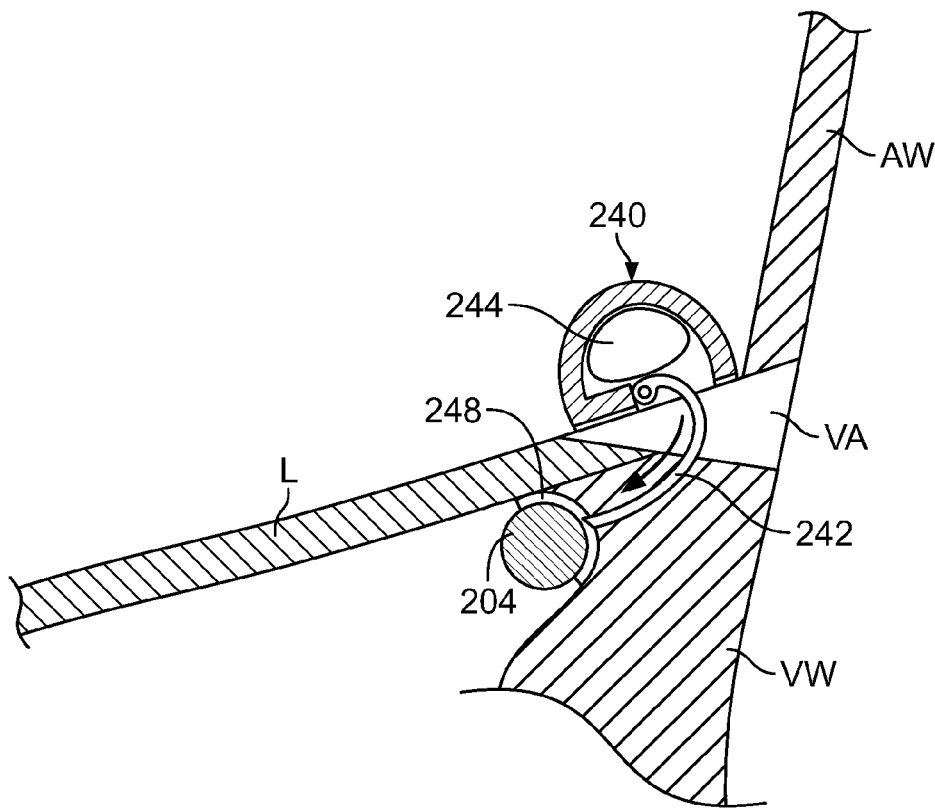

Additionally, and with reference now to FIGS. 5C and 5D, some embodiments may include one or more fasteners and fastener receiving pieces. For example, a circular hook applier 240, including multiple tethered hooks 242 on a pivot mandrel 246 and a balloon 244 may be disposed on the upper, atrial side of the valve annulus VA, and lower stabilizing member 204 may carry one or more receiving pieces 248 for receiving part of one or more of hooks 242. As shown in FIG. 5D, when balloon 244 is inflated, it drives hooks 242 in a curved path through tissue of the valve annulus VA and into receiving piece 248. Receiving piece 248 may comprise any suitable material with any configuration for receiving and holding a portion of hooks 242. In some embodiments, for example, receiving piece 248 may comprise a Dacron strip, while in other embodiments the fastener and fastener receiving piece may be configured similar to a plastic garbage bag tie or the like. Any configuration is contemplated within the scope of the invention. In alternative embodiments, anchors may be driven from lower stabilizing member 204 into a receiving piece carried by upper stabilizing member 202.

Figure 6:
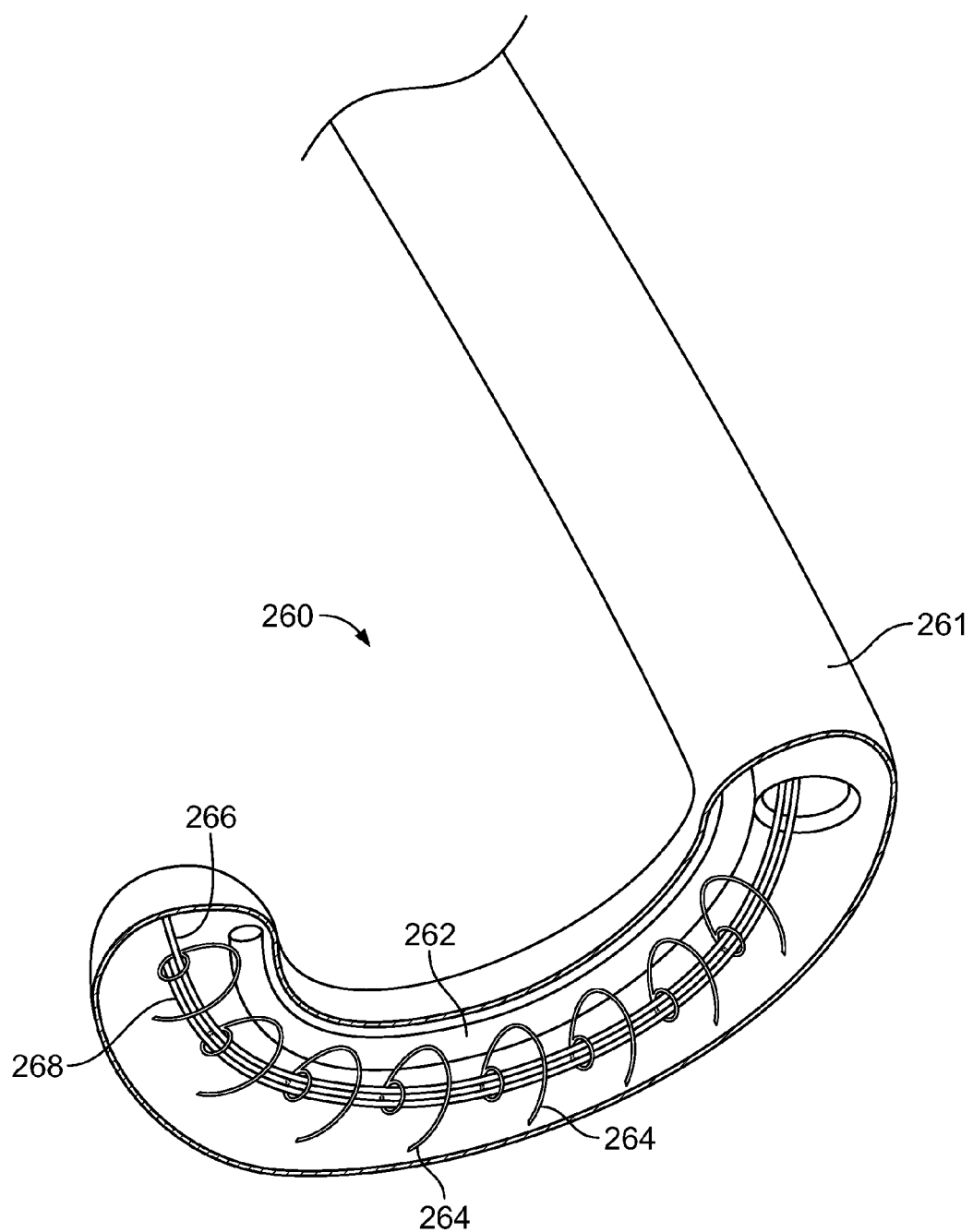
FIG. 6 is a perspective view of a balloon-driven hook applier for applying hooks to a cardiac valve annulus, according to one embodiment of the present invention.
Figure 7:
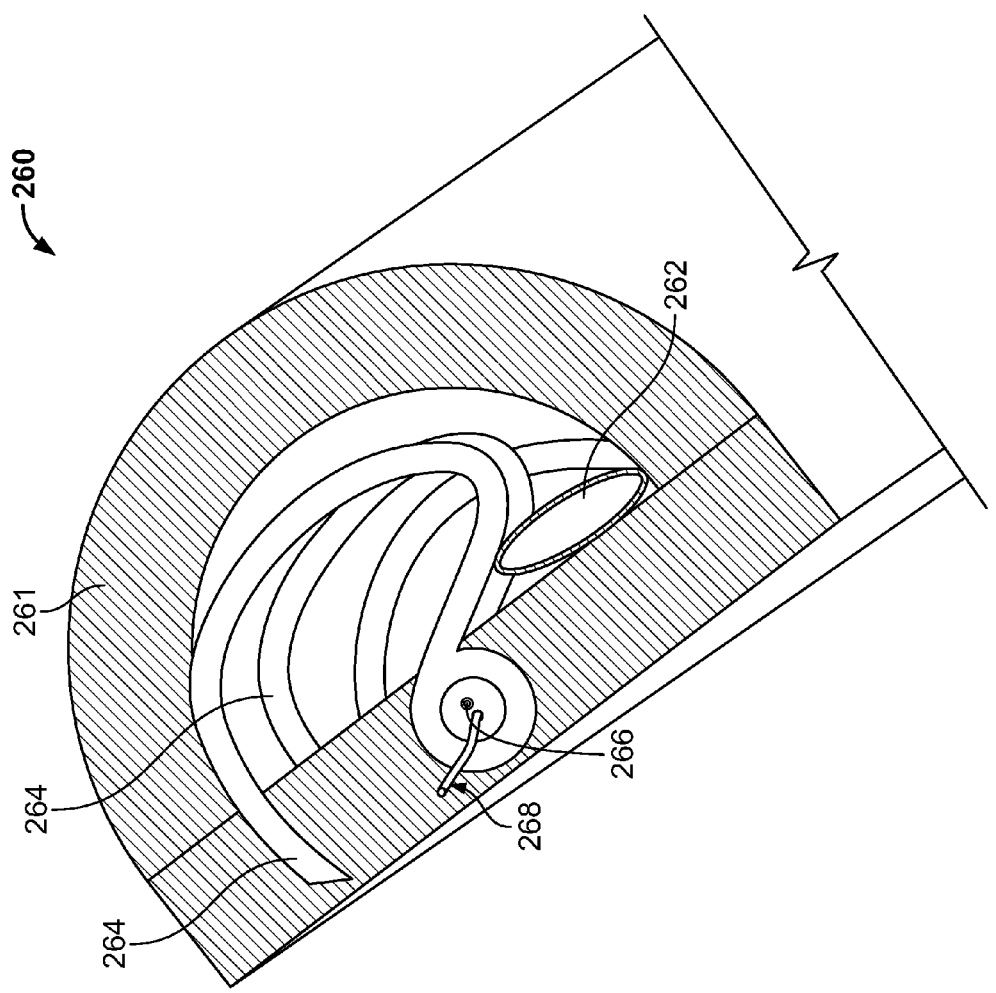
FIG. 7 is a close-up view of the device in FIG. 6.
Figure 8:
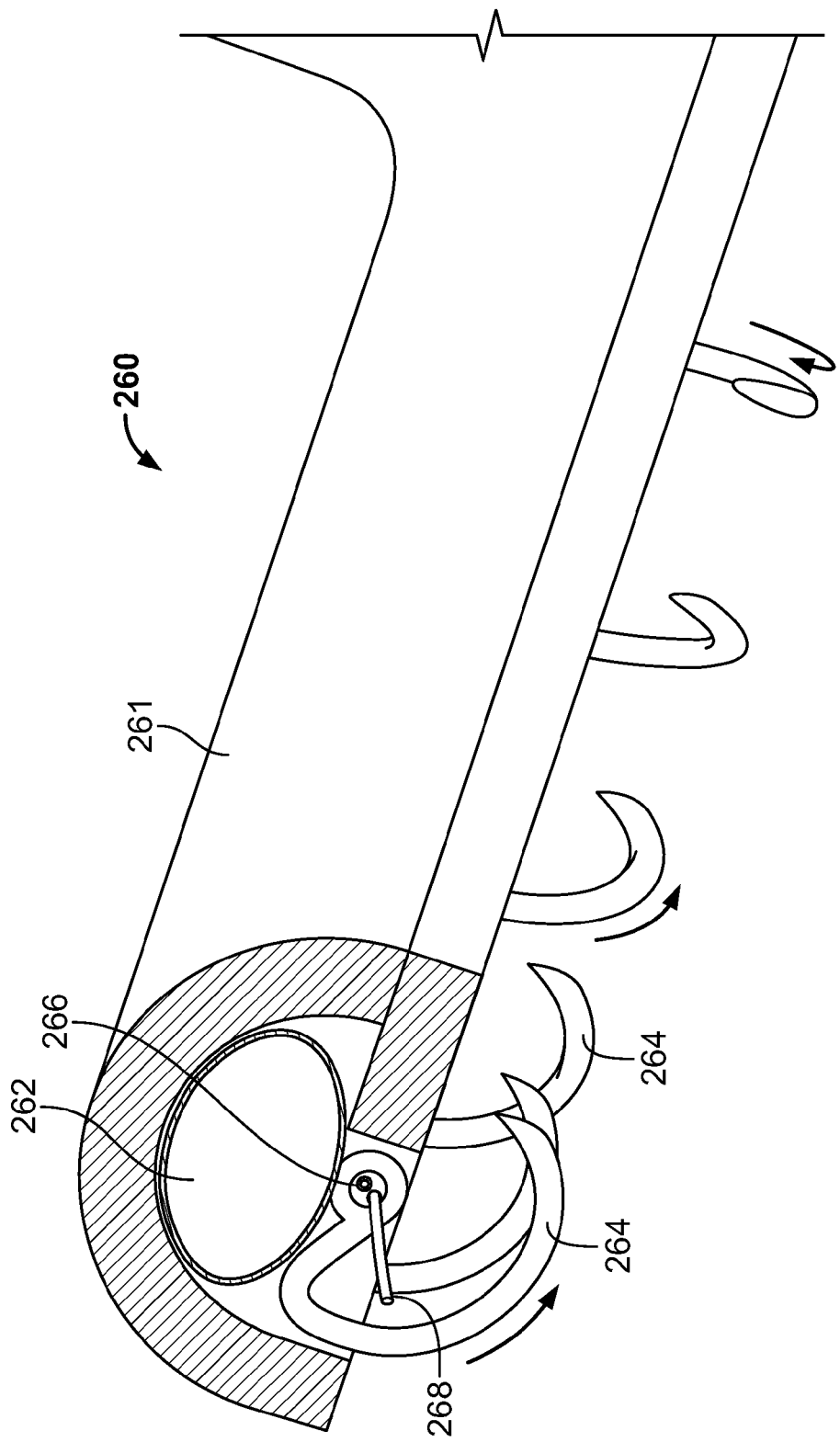
FIG. 8 is a perspective view of a balloon-driven hook applier as in FIGS. 6 and 7, with the balloon expanded and the hooks deployed, according to one embodiment of the present invention.

Referring now to FIGS. 6, 7 and 8, one embodiment of a stabilizing and hook delivery device 260 is shown. Typically, hook delivery device 260 will include an elongate housing or shaft 261, which will house a series of hooks 264 coupled to housing 261 via a pivot mandrel 266 and coupled to one another via a tether 268. Housing 262 will also include one or more expandable balloons 262 for driving hooks 264. Housing 262 may be flexible or rigid in various embodiments. Of course, any number, size and shape of hooks 264 (or other anchors) may be included in housing 261. Tether 268 may be one long piece of material or two or more pieces and may comprise any suitable material, such as suture, suture-like material, a Dacron strip or the like. Pivot mandrel 268 may also have any suitable configuration and be made of any suitable material. In one embodiment, mandrel 268 is made of a metal such as stainless steel, titanium or nitinol. Expandable balloon 262 may have any suitable size and configuration. In some embodiments, more than one balloon may be used. As shown in FIG. 8, inflating balloon 262 drives hooks 264 in a curvilinear path (arrows) into adjacent tissue (not shown). Hooks thus driven into tissue of a cardiac valve annulus may then be cinched, via tether 268, to reduce the valve diameter, thus treating or ameliorating valve regurgitation.

Although the foregoing is a complete and accurate description of the present invention, the description provided above is for exemplary purposes only, and variations may be made to the embodiments described without departing from the scope of the invention. Thus, the above description should not be construed to limit the scope of the invention as described in the appended claims.

What is claimed is:

1. A method for constricting a heart valve annulus comprising:
    introducing a stabilizing member from beneath one or more leaflets of a heart valve to a ventricular side of a heart valve annulus, wherein the stabilizing member comprises an elongate body having a proximal end, a distal end, and a longitudinal axis therebetween, the distal end having a curvature that conforms to at least a portion of the ventricular side of the annulus and adapted to deliver at least one tethered anchor enclosed therein;
    delivering the at least one tethered anchor transversely to the longitudinal axis of the stabilizing member into ventricular wall tissue, wherein the at least one tethered anchor does not penetrate into tissue of an atrium; and
    cinching the tether to reduce the circumference of at least a portion of the heart valve annulus.

2. The method of claim 1 wherein the heart valve annulus is a mitral valve annulus.

3. The method of claim 1 performed on a beating heart.

* * * * *